(12) United States Patent
Chiu et al.

(10) Patent No.: US 9,926,244 B2
(45) Date of Patent: Mar. 27, 2018

(54) PROCESS FOR DRYING HCFO-1233ZD

(71) Applicant: Honeywell International Inc., Morris Plains, NJ (US)

(72) Inventors: Yuon Chiu, Denville, NJ (US); Stephen A. Cottrell, Baton Rouge, LA (US); Hang T. Pham, Amherst, NY (US); Gustavo Cerri, Parsippany, NJ (US)

(73) Assignee: Honeywell International Inc., Morris Plains, NJ (US)

(*) Notice: Subject to any disclaimer, the term of this patent is extended or adjusted under 35 U.S.C. 154(b) by 0 days.

(21) Appl. No.: 15/368,027

(22) Filed: Dec. 2, 2016

(65) Prior Publication Data

US 2017/0081265 A1    Mar. 23, 2017

Related U.S. Application Data

(63) Continuation-in-part of application No. 15/046,591, filed on Feb. 18, 2016, now Pat. No. 9,540,296, and a continuation of application No. 14/929,657, filed on Nov. 2, 2015, which is a continuation of application No. 13/298,452, filed on Nov. 17, 2011, now Pat. No. 9,175,200, which is a continuation of application No. 12/605,609, filed on Oct. 26, 2009, now Pat. No. 8,163,196, and a continuation-in-part of application No. 12/259,694, filed on Oct. 28, 2008, now Pat. No. 7,935,268.

(60) Provisional application No. 62/135,282, filed on Mar. 19, 2015, provisional application No. 61/109,007, filed on Oct. 28, 2008.

(51) Int. Cl.
| C07C 17/38 | (2006.01) |
| C07C 17/383 | (2006.01) |
| C07C 17/389 | (2006.01) |
| C07C 21/18 | (2006.01) |

(52) U.S. Cl.
CPC ............ *C07C 17/383* (2013.01); *C07C 17/38* (2013.01); *C07C 17/389* (2013.01)

(58) Field of Classification Search
CPC ....... C07C 17/38; C07C 17/383; C07C 21/18; C09K 5/044; C09K 2205/126; C09K 2205/32
See application file for complete search history.

(56) References Cited

U.S. PATENT DOCUMENTS

| 2,739,987 A | 3/1956 | Rah |
| 2,834,748 A | 5/1958 | Bailey et al. |
| 2,846,458 A | 8/1958 | Haluska |
| 2,889,379 A | 6/1959 | Davis et al. |
| 2,917,480 A | 12/1959 | Bailey et al. |
| 4,465,786 A | 8/1984 | Zimmer et al. |
| 4,798,818 A | 1/1989 | Baizer et al. |
| 4,960,535 A | 10/1990 | Logsdon et al. |
| 4,961,870 A | 10/1990 | Cook et al. |
| 5,227,088 A | 7/1993 | Swan et al. |
| 5,283,003 A | 2/1994 | Chen |
| 6,059,860 A | 5/2000 | Larson |
| 6,221,830 B1 * | 4/2001 | Miller .................. C01B 7/0712 203/50 |
| 7,084,315 B2 | 8/2006 | Corr et al. |
| 7,438,825 B1 | 10/2008 | Chen et al. |
| 7,442,321 B1 | 10/2008 | Chen et al. |
| 7,479,238 B1 | 1/2009 | Chen et al. |
| 7,935,268 B2 | 5/2011 | Basu et al. |
| 8,067,650 B2 | 11/2011 | Wang et al. |
| 8,163,196 B2 | 4/2012 | Basu et al. |
| 8,212,092 B2 | 7/2012 | Rao et al. |
| 8,703,006 B2 | 4/2014 | Basu et al. |
| 8,802,743 B2 | 8/2014 | Basu et al. |
| 8,921,621 B2 | 12/2014 | Cottrell et al. |
| 8,946,312 B2 | 2/2015 | Basu et al. |
| 9,175,200 B2 | 11/2015 | Basu et al. |
| 9,540,296 B2 | 1/2017 | Chiu et al. |
| 2006/0180785 A1 | 8/2006 | Merchant et al. |

(Continued)

FOREIGN PATENT DOCUMENTS

| EP | 0974571 B1 | 1/2000 |
| EP | 2778151 A1 | 9/2014 |

(Continued)

OTHER PUBLICATIONS

Joffe, binary azeotropic system, (Industrial and Engineering Chemistry vo. 47, No. 12, 2533-2535).*
Wang et al, prediction of azeotropic temperature and composition for ternary system, (American Chemical Society, 1996, 49-52).*
International Search Report and Written Opinion issued in PCT/US2016/021218, dated Jun. 1, 2016.

(Continued)

*Primary Examiner* — Jafar Parsa
(74) *Attorney, Agent, or Firm* — Faegre Baker Daniels LLP

(57) ABSTRACT

The present disclosure provides separation processes that use azeotropic or azeotropic-like compositions of 1-chloro-3,3,3-trifluoropropene (HCFO-1233zd) that allow for improved recovery rates of 1-chloro-3,3,3-trifluoropropene during or after manufacturing processes. Such recovery or separation processes can utilize the unique properties of azeotropic or azeotropic-like composition with various combinations of separation techniques (e.g., distillation and decanting) that yield highly pure compositions of 1-chloro-3,3,3-trifluoropropene and simultaneously offer high yields of 1-chloro-3,3,3-trifluoropropene. Such highly pure compositions of 1-chloro-3,3,3-trifluoropropene may find useful applications in polymer technology as monomers or comonomers.

20 Claims, 2 Drawing Sheets

(56) References Cited

U.S. PATENT DOCUMENTS

| | | |
|---|---|---|
| 2007/0105738 A1 | 5/2007 | Nappa et al. |
| 2007/0112231 A1 | 5/2007 | Wilmet et al. |
| 2008/0011678 A1 | 1/2008 | Knapp |
| 2008/0313985 A1 | 12/2008 | Duncan |
| 2009/0253820 A1 | 10/2009 | Bowman et al. |
| 2009/0305876 A1 | 12/2009 | Singh et al. |
| 2010/0102273 A1 | 4/2010 | Basu et al. |
| 2010/0162738 A1 | 7/2010 | Low et al. |
| 2011/0012052 A1 | 1/2011 | Van Horn et al. |
| 2011/0041529 A1 | 2/2011 | Chen et al. |
| 2011/0105809 A1 | 5/2011 | Devic et al. |
| 2011/0172472 A1 | 7/2011 | Sakyu et al. |
| 2011/0309288 A1* | 12/2011 | Chen .................. C08J 9/149 252/68 |
| 2011/0315915 A1 | 12/2011 | Abbas et al. |
| 2012/0266750 A1 | 10/2012 | Thomas et al. |
| 2012/0296127 A1 | 11/2012 | Cottrell et al. |
| 2013/0158305 A1 | 6/2013 | Takahashi |
| 2014/0275662 A1 | 9/2014 | Kopkalli et al. |
| 2014/0357907 A1 | 12/2014 | Okamoto et al. |
| 2015/0099907 A1 | 4/2015 | Imura et al. |
| 2016/0215190 A1 | 7/2016 | Basu et al. |

FOREIGN PATENT DOCUMENTS

| | | |
|---|---|---|
| WO | 2008121776 A1 | 10/2008 |
| WO | 2009114397 A2 | 9/2009 |
| WO | 2009140231 A2 | 11/2009 |

OTHER PUBLICATIONS

Kim et al., "A Study to Determine the Existence of an Azeotropic R-22 "Drop-In" Substitute," Prepared by U.S. Department of Commerce for Electric Power Research Institute, Mar. 1996, pp. 1-45, U.S.

Morrison et al., "Azeotropy in Refrigerant Mixtures," International Journal of Refrigeration, 1993, vol. 16, No. 2, pp. 129-138 (Oct. 1991).

* cited by examiner

PROCESS FOR DRYING HCFO-1233ZD

CROSS-REFERENCE TO RELATED APPLICATIONS

This application is a continuation-in-part to U.S. patent application Ser. No. 15/046,591, filed on Feb. 18, 2016, which claims domestic priority from commonly owned U.S. Provisional Patent Application Ser. No. 62/135,282, filed Mar. 19, 2015; and this application is also a continuation-in-part of U.S. patent application Ser. No. 14/929,657, filed on Nov. 2, 2015, which is a continuation of U.S. application Ser. No. 13/298,452, filed Nov. 17, 2011, now U.S. Pat. No. 9,175,200, which is a continuation of U.S. application Ser. No. 12/605,609, filed Oct. 26, 2009, now U.S. Pat. No. 8,163,196, which claims the priority benefit of U.S. Provisional Application No. 61/109,007, filed Oct. 28, 2008, and which is also a continuation-in-part (CIP) of U.S. application Ser. No. 12/259,694, filed Oct. 28, 2008, now U.S. Pat. No. 7,935,268, the disclosure of each of which are hereby incorporated herein by reference in their entirety.

FIELD OF THE DISCLOSURE

In the commercial production of 1-chloro-3,3,3-trifluoropropene (HCFO-1233zd) the crude product from the process may require aqueous washing to remove HF, HCl, and other acidic components. The present disclosure pertains to azeotropic or azeotrope-like compositions of HFO-1233zd and water and processing such compositions.

BACKGROUND

Commercial uses for HCFO-1233zd (1233zd) include foam blowing agent and solvent applications. In such applications, tight control of moisture content is typically needed to meet customer requirements. Occasionally, due to process issues, the moisture level in 1233zd may exceed specification limits.

Various 1233zd production processes have been disclosed. One example is shown in U.S. Pat. No. 8,921,621, which disclosed a process for the production of HCFO-1233zd comprising the steps of: (a) reacting HCC-240 and HF in a high pressure liquid phase reactor, with subsequent steps including step (h) of "feeding the overhead crude HCFO-1233zd stream to a caustic scrubber to remove any remaining acidity and drying the scrubbed stream with a drying agent . . . ."

In the '621 process, one objective is to provide enough drying agent to remove the water in the process stream, and one must be prepared that the overhead crude HCFO-1233zd vapor stream could be fully saturated with water. In such a case, it is estimated that for every 1,000 pounds of HCFO-1233zd vapor produced, one could need to remove at least 4 pounds of water. Accordingly, if using a typical molecular sieve desiccant, which can adsorb up to about 15 wt. % moisture, one would need to use up to about 27 pounds of molecular sieve for every 1,000 pounds of HCFO-1233zd generated in the process. The embodiments in this disclosure have the added benefit of significantly reducing the desiccant consumption required for such a process and utilizing the benefits of azeotropic or azeotrope-like compositions of 1-chloro-3,3,3-trifluoropropene and water.

SUMMARY

The present disclosure provides separation processes that use azeotropic or azeotropic-like compositions of 1-chloro-3,3,3-trifluoropropene (HCFO-1233zd) that allow for improved recovery rates of 1-chloro-3,3,3-trifluoropropene during or after manufacturing processes. Such recovery or separation processes can utilize the unique properties of azeotropic or azeotropic-like compositions with various combinations of separation techniques (e.g., distillation and decanting) that yield highly pure compositions of 1-chloro-3,3,3-trifluoropropene and simultaneously offer high yields of 1-chloro-3,3,3-trifluoropropene. Such highly pure compositions of 1-chloro-3,3,3-trifluoropropene may find useful applications in polymer technology as monomers or comonomers.

Methods for recovering 1-chloro-3,3,3-trifluoropropene may include forming an azeotropic or azeotrope-like composition comprising, consisting essentially of, or consisting of 1-chloro-3,3,3-trifluoropropene and water, conveying the formed azeotropic or azeotrope-like composition into a separator, and recovering an organic layer comprising 1-chloro-3,3,3-trifluoropropene. In various embodiments, the composition may comprise as little as about 70 wt. % 1-chloro-3,3,3-trifluoropropene, 86 wt. % 1-chloro-3,3,3-trifluoropropene, 90% wt. % 1-chloro-3,3,3-trifluoropropene, as great as 98.5 wt. % 1-chloro-3,3,3-trifluoropropene, 99 wt. % 1-chloro-3,3,3-trifluoropropene, 99.95 wt. % 1-chloro-3,3,3-trifluoropropene, or within any range defined between any two of the foregoing values (such as between 70 wt. % 1-chloro-3,3,3-trifluoropropene and 99.95 wt. % 1-chloro-3,3,3-trifluoropropene) and as little as 0.05 wt. % water, 2.5 wt. % water, 10 wt. % water, or as great as 14 wt. % water, 20 wt. % water, 30 wt. % water, or within any range defined between any two of the foregoing values (such as between 0.05 wt. % water and 30 wt. % water). In some embodiments, the compositions may have a boiling point of about 17.4° C.±1° C. at a pressure of about 14.7 psia.

Various methods may also include additional steps, such as decanting off a water layer, returning the organic layer to a distillation column, and/or separating water in the organic layer from 1-chloro-3,3,3-trifluoropropene with distillation.

Also disclosed are methods that include providing a mixture of 1-chloro-3,3,3-trifluoropropene and water, allowing the mixture to separate into an organic layer including mostly 1-chloro-3,3,3-trifluoropropene and an aqueous layer, decanting a portion of the aqueous layer from the mixture, conveying the organic layer to a distillation column, forming an azeotropic mixture of 1-chloro-3,3,3-trifluoropropene and water in the distillation column, removing the azeotropic mixture from the distillation column as an overhead stream, and removing substantially pure 1-chloro-3,3,3-trifluoropropene from the bottoms of the distillation column.

In various embodiments, some methods may result in a substantially pure 1-chloro-3,3,3-trifluoropropene, when removed from the distillation column, and may contain less than about 100 ppm of water by weight, contain less than about 50 ppm of water by weight, or contain less than about 40 ppm of water by weight. In some embodiments, the substantially pure 1-chloro-3,3,3-trifluoropropene, when removed from the distillation column, and may contain as little as about 10 ppm, 11 ppm, 15 ppm, or as great as 20 ppm, 25 ppm, 30 ppm, 40 ppm, 50 ppm, 100 ppm, or within any range defined between any two of the foregoing values (such as between 10 ppm and 40 ppm).

The azeotropic mixtures may have as little as about 70 wt. % 1-chloro-3,3,3-trifluoropropene, 86 wt. % 1-chloro-3,3,3-trifluoropropene, 90% wt. % 1-chloro-3,3,3-trifluoropropene, as great as 98.5 wt. % 1-chloro-3,3,3-trifluoropropene, 99 wt. % 1-chloro-3,3,3-trifluoropropene, 99.95 wt. %

1-chloro-3,3,3-trifluoropropene, or within any range defined between any two of the foregoing values (such as between 70 wt. % 1-chloro-3,3,3-trifluoropropene and 99.95 wt. % 1-chloro-3,3,3-trifluoropropene) and as little as 0.05 wt. % water, 2.5 wt. % water, 10 wt. % water, or as great as 14 wt. % water, 20 wt. % water, 30 wt. % water, or within any range defined between any two of the foregoing values (such as between 0.05 wt. % water and 30 wt. % water) based on the combined weight of water and 1-chloro-3,3,3-trifluoropropene. The azeotropic mixtures may have a boiling point of about 17.4° C.±1° C. at a pressure of about 14.7 psia.

Also disclosed are azeotropic or azeotrope-like compositions having 1-chloro-3,3,3-trifluoropropene and water. In some embodiments, the compositions may consist of only water and 1-chloro-3,3,3-trifluoropropene.

The compositions may have as little as about 70 wt. % 1-chloro-3,3,3-trifluoropropene, 86 wt. % 1-chloro-3,3,3-trifluoropropene, 90% wt. % 1-chloro-3,3,3-trifluoropropene, as great as 98.5 wt. % 1-chloro-3,3,3-trifluoropropene, 99 wt. % 1-chloro-3,3,3-trifluoropropene, 99.95 wt. % 1-chloro-3,3,3-trifluoropropene, or within any range defined between any two of the foregoing values (such as between 70 wt. % 1-chloro-3,3,3-trifluoropropene and 99.95 wt. % 1-chloro-3,3,3-trifluoropropene) and as little as 0.05 wt. % water, 2.5 wt. % water, 10 wt. % water, or as great as 14 wt. % water, 20 wt. % water, 30 wt. % water, or within any range defined between any two of the foregoing values (such as between 0.05 wt. % water and 30 wt. % water). In various embodiments, the composition may have a boiling point of about 17.4° C.±1° C. at a pressure of about 14.7 psia.

BRIEF DESCRIPTION OF THE DRAWINGS

The above mentioned and other features and objects of this disclosure, and the manner of attaining them, will become more apparent and the disclosure itself will be better understood by reference to the following description of exemplary embodiments of the disclosure taken in conjunction with the accompanying drawings, wherein.

Although the drawings represent embodiments of the present disclosure, the drawings are not necessarily to scale and certain features may be exaggerated in order to better illustrate and explain the present disclosure. The exemplification set out herein illustrates exemplary embodiments of the disclosure, in various forms, and such exemplifications are not to be construed as limiting the scope of the disclosure in any manner.

DETAILED DESCRIPTION

As briefly described above, this disclosure provides separation techniques that utilize azeotropic or azeotrope-like compositions of 1-chloro-3,3,3-trifluoropropene (HCFC-1233zd) and water and methods of recovering 1-chloro-3,3,3-trifluoropropene (HCFC-1233zd) from azeotropic or azeotrope-like compositions comprising 1-chloro-3,3,3-trifluoropropene and water.

1-chloro-3,3,3-trifluoropropene forms azeotropic and azeotrope-like compositions or mixtures with water, and more particularly, forms heterogeneous azeotropic and azeotrope-like composition or mixtures with water.

1-chloro-3,3,3-trifluoropropene has a boiling point of about 19° C., has a vapor pressure of 1516 hPa at about 30° C., and has the following structure:

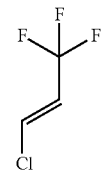

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

As described above, U.S. Pat. No. 8,921,621 describes a process for the production of 1-chloro-3,3,3-trifluoropropene (HCFC-1233zd) on a commercial scale from the reaction of 1,1,1,3,3-pentachloropropane (HCC-240fa) and HF.

In one embodiment of the '621 process, HCC-240fa and HF are fed to a liquid phase reactor operating at high pressure. The resulting product stream of 1233zd, HCl, HF, and other byproducts is partially condensed to recover HF by phase separation. The recovered HF phase is recycled to the reactor. The HCl is scrubbed from the vapor stream and recovered as an aqueous solution. The remaining organic components including the desired HCFC-1233zd are scrubbed, dried and distilled to meet commercial product specifications.

Figure 1:
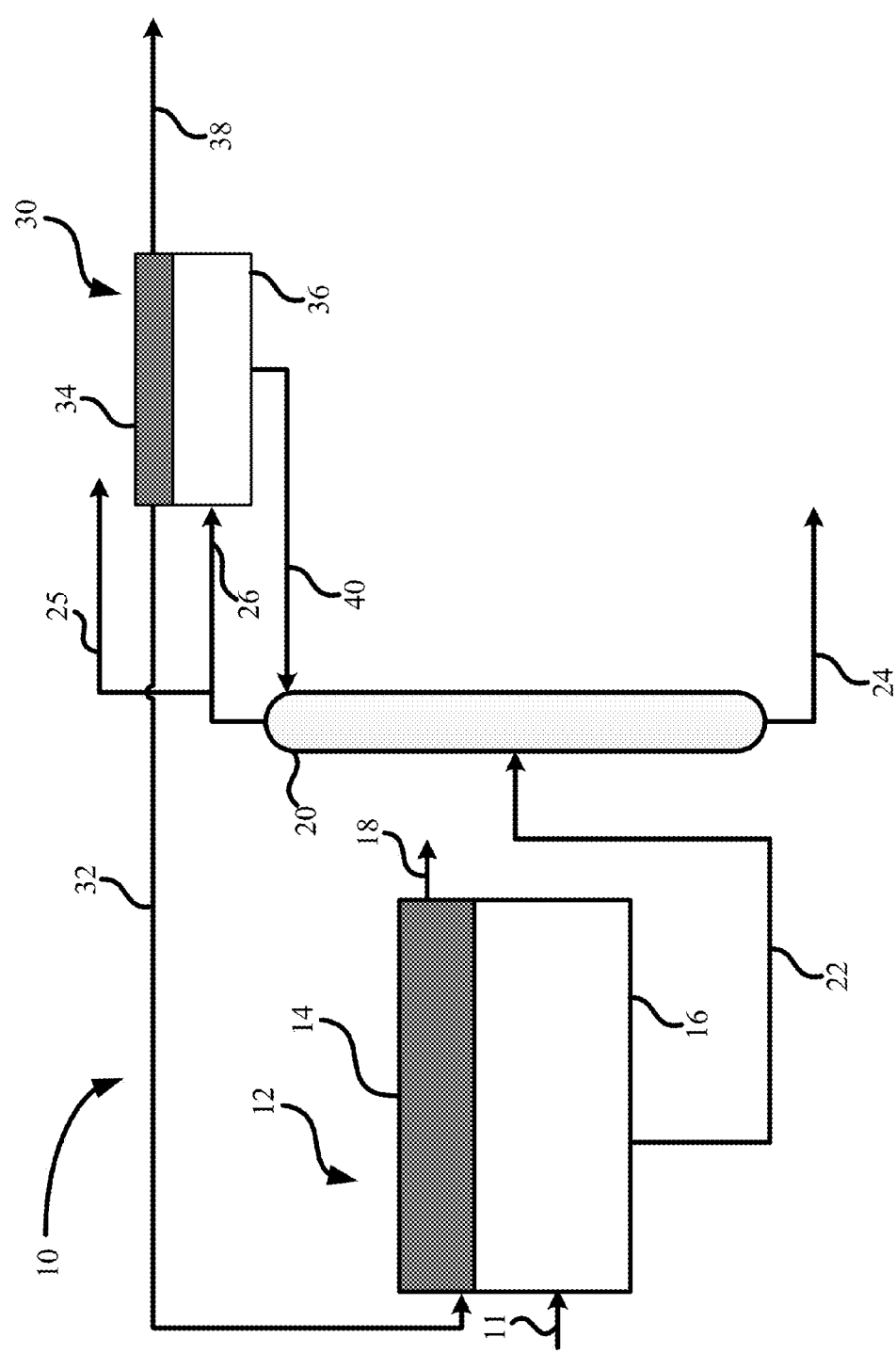
FIG. 1 is a process diagram for the recovery of 1-chloro-3,3,3-trifluoropropene.

FIG. 1 is a process diagram for the recovery of 1-chloro-3,3,3-trifluoropropene from water. In one embodiment, wet and acid-free 1233zd (HCFO-1233zd) crude vapor from the caustic scrubber outlet are condensed in a condenser. The condensed wet 1233zd will then flow (illustrated in FIG. 1 as flow stream 11) into a distillation pump tank or decanting tank 12, where the water will settle as the top layer (first aqueous layer 14) and the 1233zd will settle as bottom layer (first organic layer 16). At a production rate of 1000 to 1500 lbs/hr of 1233zd, including scrubber liquid entrainment, it is expected that about 2 gals/hr of free water will accumulate in the distillation pump tank (capacity of 19,000 gallons). Accordingly, it is estimated that the tank 12 can easily handle about 4,000 gal of free water, at least temporarily.

During commercial processing of 1233zd, it is expected that one should not need to attend to this water for up to 3 months at 1,500 lbs/hr crude 1233zd production rate and when water is removed, it may be removed as first removal stream 18. The removal of water as first removal stream 18 may be accomplished by decanting, selective pumping, or other liquid-liquid separating processes. A monitoring program to track this water volume, and its acidity content, e.g., to prevent any corrosion or overspill incident, has been developed. The water is expected to contain about 2,000 ppm crude 1233zd, or about 0.03 lbs/hr organic. As used herein, the term "ppm" or "parts-per-million" shall be understood to be the mass fraction unless explicitly stated otherwise. This water can be recycled to the caustic scrubber for organic recovery and disposal.

The first organic layer 16 may then be further processed, such as by distilling the first organic layer. Thus, first organic layer 16 may flow through distillation inlet 22 to distillation column 20, where the 1-chloro-3,3,3-trifluoropropene and water may be distilled, including being distilled until forming an azeotrope.

As used herein, distillation column 20 can be understood to include any conventional fractionating column or fractionation column that uses distillation to separate a mixture into component parts or fractions based on differences in volatilities. Thus, the first organic layer 16 may be distilled in distillation column, yielding a bottoms 24 of essentially pure 1-chloro-3,3,3-trifluoropropene while overhead 26 may be condensed and sent either to the first separator 12 and/or to a second phase separator 30. In various embodiments, the top vapor fraction or overhead 26 may be an azeotropic or azeotrope-like composition of 1-chloro-3,3,3-trifluoropropene and water.

It should be noted that, in some embodiments, other organics and/or impurities (e.g., 1,3,3,3-tetrafluoropropene (HFO-1234ze)) may also be present and/or may also form an azeotrope with the water in the overhead of the distillation column. In some embodiments, other other organics and/or impurities in the composition which themselves form azeotropes with water may be used to advantageously further draw additional water from the contents of the distillation column 21 in addition to the water which is drawn into the principal azeotrope of 1-chloro-3,3,3-trifluoropropene and water, further drying and purifying the 1233zd collected product. Additionally, relatively low boiling point impurities, even when not themselves able to form azeotropes with water, may nevertheless volatilize and thereby be removed in the overhead stream. Thus, in the present process, both water-containing azeotropes of impurities and/or non-azeotropic compositions of impurities may be drawn away from 1233zd in the distillation column 20 to enhance the purity of the recovered 1233zd.

Furthermore, in some embodiments, excess 1-chloro-3,3,3-trifluoropropene may be present in azeotrope composition in the overhead, for example, due to tray inefficiencies or distillation column inefficiencies.

The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. As disclosed herein, an azeotrope is a liquid mixture that exhibits a maximum or minimum boiling point relative to the boiling points of surrounding mixture compositions. Also, as used herein, the term "azeotrope-like" refers to compositions that are strictly azeotropic and/or that generally behave like azeotropic mixtures.

An azeotrope or an azeotrope-like composition is an admixture of two or more different components which, when in liquid form under a given pressure, will boil at a substantially constant temperature, which temperature may be higher or lower than the boiling temperatures of the individual components and which will provide a vapor composition essentially identical to the liquid composition undergoing boiling.

As used herein, azeotropic compositions may be defined to include azeotrope-like compositions, which is a composition that behaves like an azeotrope, i.e., that has constant boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

In various embodiments is this disclosure, a composition which comprises effective amounts of 1-chloro-3,3,3-trifluoropropene and water to form an azeotropic or azeotrope-like composition is provided. As used herein, the term "effective amount" is an amount of each component which, when combined with the other component, results in the formation of an azeotrope or azeotrope-like mixture.

The compositions preferably are binary azeotropes which comprise or consist essentially of combinations of 1-chloro-3,3,3-trifluoropropene and water, or consist of combinations of 1-chloro-3,3,3-trifluoropropene and water. As used herein, the term "consisting essentially of", with respect to the components of an azeotrope-like composition or mixture, means the composition contains the indicated components in an azeotrope-like ratio, and may contain additional components provided that the additional components do not form new azeotrope-like systems. For example, azeotrope-like mixtures consisting essentially of two compounds are those that form binary azeotropes, which optionally may include one or more additional components, provided that the additional components do not render the mixture non-azeotropic and do not form an azeotrope with either or both of the compounds (e.g., do not form a ternary azeotrope).

As used herein, the terms "heteroazeotrope" and "heterogeneous azeotrope" mean an azeotrope-like composition comprising a vapor phase existing concurrently with two liquid phases.

The present disclosure also encompasses generating an azeotropic or azeotrope-like composition of 1-chloro-3,3,3-trifluoropropene and water followed by isolating the azeotrope from impurities. The present disclosure also includes steps for separating and purifying 1-chloro-3,3,3-trifluoropropene from the azeotropic mixture, as discussed in greater detail below.

1-chloro-3,3,3-trifluoropropene may be produced using one or more methods that are known in the art, in which 1-chloro-3,3,3-trifluoropropene is produced as a component of a reactant mixture containing one or more impurities.

Post-purification, it also may be desirable to separate the component parts of the 1-chloro-3,3,3-trifluoropropene and water azeotrope to a purified form of 1-chloro-3,3,3-trifluoropropene which is essentially water-free. As used herein, "essentially water-free" or "water-free" refers to compositions of 1-chloro-3,3,3-trifluoropropene which include less than 1.0 wt. % water. For example, compositions of 1-chloro-3,3,3-trifluoropropene and water that have less than 0.4 wt. % water, or less than 0.1 wt. % water, would be considered to be water-free.

Separation methods may include any method generally known in the art. In one embodiment, for example, the excess water can be removed from the 1-chloro-3,3,3-trifluoropropene by liquid-liquid phase separation, though other alternatives include distillation or scrubbing. The remaining water can then be removed from the 1-chloro-3,3,3-trifluoropropene by distillation and/or the use of one or more drying media or desiccants such as molecular sieves, calcium sulfate, silica, alumina, and combinations thereof.

Figure 2:
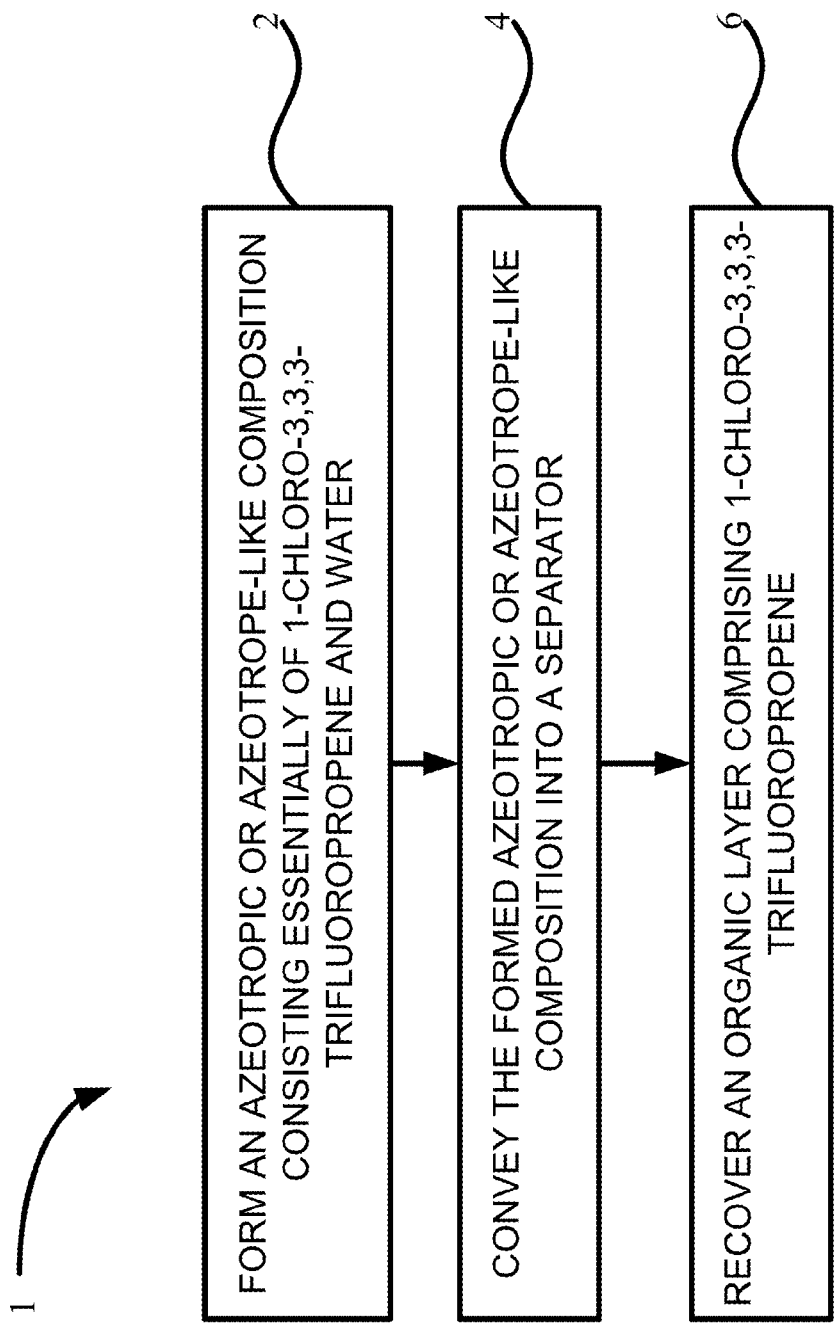
FIG. 2 is a flow diagram of an exemplary method for recovering 1-chloro-3,3,3-trifluoropropene.

Exemplary methods, such as those illustrated in the flow diagram of FIG. 2, can be used for recovering 1-chloro-3,3,3-trifluoropropene. Recovery method 1 may include forming an azeotropic or azeotrope-like composition consisting essentially of 1-chloro-3,3,3-trifluoropropene and water (step 2), conveying the formed azeotropic or azeotrope-like composition into a separator (step 3), and recovering an organic layer comprising 1-chloro-3,3,3-trifluoropropene (step 4).

For example, with continued reference to FIG. 1, the overhead may be split, before or after condensing, into a light organics purge 25 and an overhead products stream 26, which may have an azeotropic composition of water and 1-chloro-3,3,3-trifluoropropene, and may be condensed and sent to a second phase separator 30. In some embodiments, the light organics purge may be part of second phase separator 30. Light organics purge may be used to remove light organics present in production systems and may include compounds such as 1,3,3,3-tetrafluoropropene (HFO-1234ze) isomers, 1,1,1,3,3-pentafluoropropane (HFC-245fa) and, in some cases, some HFO-1233zd.

Here, with overhead products stream 26 flowing into separator 30, a second water phase 34 and a second organic layer 36 may form. The second water phase 34 may be decanted off and discarded (illustrated second discard stream 38) or may be recycled (in whole or in part) to first phase separator 12 via recycle stream 32. In various embodiments, the exemplary process 10 may allow for greater yields of 1-chloro-3,3,3-trifluoropropene at higher purities. In some embodiments, second organic layer 36 may have other organic compounds, in addition to 1-chloro-3,3,3-trifluoropropene. For example, in some embodiments, reflux stream 40 from second organic layer may comprise significant amounts of 1,3,3,3-tetrafluoropropene (HFO-1234ze), 1,1,1,3,3-pentafluoropropane (HFC-245fa), and/or other impurities (e.g., about 70 wt. % HFO-1234ze, about 15 wt. % HFC-245fa, and about 15 wt. % 1-chloro-3,3,3-trifluoropropene Purified 1-chloro-3,3,3-trifluoropropene removed from distillation column 20 as bottoms stream 24 may include less than 50 ppm, less than 40 ppm, less than 25 ppm, less than 20 ppm, or 10 ppm or less, of water or, in other embodiments, may include as little as 10 ppm, 15, ppm, or 20 ppm, or as great as 25 ppm, 40 ppm, or 50 ppm of water, or any amount of water within any range defined between any two of the foregoing values. The purified 1-chloro-3,3,3-trifluoropropene (1233zd) may be used as an end product such as a refrigerant, blowing agent, propellant, or diluent for gaseous sterilization, or it may be used as a monomer, as an intermediate, or otherwise further processed for the production of alternative HFOs or similar compounds.

Also, the purified azeotrope meets the current need in the art for mixtures that have no ozone depletion potential and are negligible contributors to greenhouse global warming and are nonflammable. Such a mixture may be utilized in a wide range of uses such as, but not limited to, refrigerants, blowing agents, propellants and diluents for gaseous sterilization. The azeotrope may be provided in combination with other useful additives or ingredients for such purposes.

EXAMPLES

Example 1—Processing of 1,000 lbs of Crude HCFO-1233zd 1,000 lbs of wet and acid-free crude HCFO-1233zd vapor from the caustic scrubber outlet is condensed in a condenser. The condensed wet HCFO-1233zd will then flow into a decanter. The water will settle as top layer while the HCFO-1233zd will settle as bottom layer.

The top water layer is withdrawn and expected to have about 4 lbs of water and to contain about 2,000 ppm of dissolved HCFO-1233zd or 0.008 lbs. This water can be recycled to the caustic scrubber for organic recovery or be disposed.

The bottom HCFO-1233zd organic layer is withdrawn and expected to have about 1,000 lbs of HCFO-1233zd and to contain about 400 ppm of dissolved water or 0.4 lbs. This resulting HCFO-1233zd stream is then dried with a drying agent such as molecular sieve 3A or 4A, activated alumina, silica gel, $CaSO_4$, and the like.

Using a commercial 3A molecular sieve desiccant which can adsorb up to 15% moisture, this improved process would have consumed only 2.7 pounds of molecular sieve for every 1,000 pounds of HCFO-1233zd processed. The water content is about 10 ppm after this treatment.

In view of this low desiccant consumption rate, the drying equipment size can be made much smaller than those used in prior art processing. Furthermore, given that the molecular sieve can be regenerated, the ultimate drying agent consumption can be minimized.

Example 2—Processing 1,000 lbs of Crude HCFO-1233zd 1,000 lbs of liquid crude HCFO-1233zd containing 10 lbs of HF acid is mixed with about 300 lbs of water and/or diluted caustic solution and then washed to remove the acid at sub-cooled temperature while maintaining the mixture in a liquid phase. The resulting wet and acid free HCFO-1233zd will then flow into a decanter. The water or caustic solution will settle as top layer while the HCFO-1233zd will settle as bottom layer. The above can be carried out stagewise (e.g., first washing with water and decanting, then followed by washing with aqueous caustic and decanting, etc.).

The top water or caustic layer is withdrawn and expected to have about 300 lbs of water and to contain about 2,000 ppm of dissolved HCFO-1233zd or 0.6 lbs. This water or caustic solution can subsequently be heated or stripped to recover valuable organic or be disposed.

The bottom HCFO-1233zd organic layer is withdrawn and expected to have about 1,000 lbs of HCFO-1233zd and to contain about 400 ppm of dissolved water or 0.4 lbs. This resulting HCFO-1233zd stream is then dried with a drying agent such as molecular sieve 3A or 4A, activated alumina, silica gel, $CaSO_4$, and the like.

Using a commercial 3A molecular sieve desiccant which can adsorb up to 15% moisture, this improved process would have consumed only 2.7 pounds of mole sieve for every 1,000 pounds of HCFO-1233zd processed. The water content is about 10 ppm after this treatment.

In view of this low desiccant consumption rate, the drying equipment size can be made much smaller than those used in prior art processing. Furthermore, given that the molecular sieve can be regenerated, the ultimate drying agent consumption can be minimized.

Example 3—Processing of Crude 1233zd in a Pilot Plant 100 lbs of wet and acid-free crude HCFO-1233zd vapor from the caustic scrubber outlet is condensed in a condenser. The condensed wet HCFO-1233zd will then flow into a decanter. The water will settle as top layer while the HCFO-1233zd will settle as bottom layer.

The top water layer is withdrawn and discarded.

The bottom HCFO-1233zd organic layer is withdrawn. This resulting HCFO-1233zd stream is then dried with a drying agent such as molecular sieve 3A or 4A, activated alumina, silica gel, $CaSO_4$, and the like.

Using a commercial 3A molecular sieve desiccant which can adsorb up to 15% moisture, this improved process would have consumed only 2.7 pounds of molecular sieve for every 1,000 pounds of HCFO-1233zd processed. The water content is about 10 ppm after this treatment.

Alternatively, the organic layer may be further processed, such as by forming an azeotropic or azeotrope-like composition to further separate water and 1-chloro-3,3,3-trifluoropropene.

For Example 4 and Example 5 below, 1,000 lbs/hr of wet and acid-free 1-chloro-3,3,3-trifluoropropene vapor was condensed in a condenser. The condensed 1-chloro-3,3,3-trifluoropropene along with 100 lbs/hr of wet azeotropic 1-chloro-3,3,3-trifluoropropene and water from a distillation column were combined. The resulting mixture was then sent to a phase separator. Water settled as the top layer while the 1-chloro-3,3,3-trifluoropropene settled as the bottom (organic) layer. The water layer contained 2,000 ppm crude 1-chloro-3,3,3-trifluoropropene or about 0.2 lbs/hr organic. The water layer containing 1-chloro-3,3,3-trifluoropropene was then processed as below according to Example 4 and Example 5.

Example 4—Recovery of 1-chloro-3,3,3-trifluoropropene from Water 1,100 lbs/hr of a mixture of crude 1-chloro-3,3,3-trifluoropropene and 0.4 lbs/hr water was fed into a distillation column, where essentially all of the water was distilled in the overhead along with about 100 lbs/hr of the 1-chloro-3,3,3-trifluoropropene. The overhead was found to be an azeotropic mixture of 1-chloro-3,3,3-trifluoropropene and water.

This overhead mixture was then sent to a phase separator or caustic scrubber to re-separate out the water from the 1-chloro-3,3,3-trifluoropropene contained in the overhead.

The bottom stream yielded about 1,000 lbs/hr of crude 1-chloro-3,3,3-trifluoropropene containing about 50 ppm moisture of less.

Example 5—Recovery of 1-chloro-3,3,3-trifluoropropene from Water 1,100 lbs/hr of crude 1-chloro-3,3,3-trifluoropropene and 0.4 lbs/hr of water was fed into a distillation column where essentially all of the 0.4 lbs/hr of water and about 100 lbs/hr of azeotropic crude 1-chloro-3,3,3-trifluoropropene was contained in the overhead. The overhead azeotropic mixture was then sent to a second phase separator, forming water phase and organic phase. The top layer was found to contain the 0.4 lb/hr of water and may either be recycled back to the first phase separator, may be discarded, or may be partially recycled. The water phase of first phase separator may also be discarded or sent for further processing. The organic phase was then returned to the distillation column as reflux. When used with the second phase separator, the bottoms was found to yield nearly 100% 1-chloro-3,3,3-trifluoropropene, whereas the reflux stream 40 was found to contain about 50 ppm of water.

In additional trial runs, the composition of the bottoms stream was able to be controlled to yield between 11 ppm by weight water to about 90 ppm by weight water. Thus, a substantially pure and dry 1-chloro-3,3,3-trifluoropropene was removed from the distillation column.

Thus, as can be seen from the above examples, azeotropic or azeotropic-like compositions of 1-chloro-3,3,3-trifluoropropene and water can be used to recover 1-chloro-3,3,3-trifluoropropene in an economical fashion.

Example 6—Azeotropic Data for 1-chloro-3,3,3-trifluoropropene and Water

An ebulliometer consisting of vacuum jacketed tube with a condenser on top which was further equipped with a Quartz Thermometer was used. About 10 cc of trans-HFO-1233zd was charged to the ebulliometer and then water was added in small, measured increments. Temperature depression was observed when water was added, indicating a binary minimum boiling azeotrope had been formed. From greater than 0 to about 30 weight percent water, the boiling point of the composition changes less than about 0.5° C. at ambient pressure.

| Temp (° C.) | Wt. % 1-chloro-3,3,3-trifluoropropene | Wt. % Water |
| --- | --- | --- |
| 17.9 | 100 | 0 |
| 17.7 | 99.7 | 1.4 |
| 17.5 | 98.6 | 2.6 |
| 17.5 | 95.8 | 5.3 |
| 17.4 | 93.2 | 7.9 |
| 17.4 | 90.7 | 10.3 |
| 17.4 | 87.5 | 13.6 |
| 17.4 | 84.4 | 16.5 |
| 17.4 | 81.6 | 19.3 |
| 17.4 | 79.0 | 21.9 |
| 17.4 | 76.5 | 24.4 |
| 17.4 | 74.2 | 26.7 |
| 17.4 | 72.0 | 28.8 |
| 17.4 | 69.9 | 30.9 |

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed.

Where a range of numerical values is recited herein, unless otherwise stated, the range is intended to include the endpoints thereof, and all integers and fractions within the range. It is not intended that the scope of the invention be limited to the specific values recited when defining a range.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A method for recovering 1-chloro-3,3,3-trifluoropropene comprising,
    forming an azeotropic or azeotrope-like composition comprising 1-chloro-3,3,3-trifluoropropene and water;
    conveying the formed azeotropic or azeotrope-like composition into a separator; and
    recovering an organic layer comprising 1-chloro-3,3,3-trifluoropropene.

2. The method of claim 1, wherein the composition comprises from about 0.05 wt. % to about 30 wt. % water and from about 70 wt. % to about 99.95 wt. % 1-chloro-3,3,3-trifluoropropene, based on the combined weight of water and 1-chloro-3,3,3-trifluoropropene.

3. The method of claim 1, wherein the composition has a boiling point of about 17.4° C.±1° C. at a pressure of about 14.7 psia.

4. The method of claim 1, wherein the recovering step further comprises decanting off a water layer.

5. The method of claim 1, further comprising the additional step of returning the organic layer to a distillation column.

6. The method of claim 5, further comprising the additional step of separating water in the organic layer from 1-chloro-3,3,3-trifluoropropene with distillation.

7. The method of claim 1, wherein the azeotropic or azeotrope-like composition consists essentially of 1-chloro-3,3,3-trifluoropropene and water.

8. The method of claim 7, wherein the azeotropic or azeotrope-like composition consists of 1-chloro-3,3,3-trifluoropropene and water.

9. A method comprising:
    providing a mixture of 1-chloro-3,3,3-trifluoropropene and water;
    allowing the mixture to separate into an organic layer including mostly 1-chloro-3,3,3-trifluoropropene and an aqueous layer;
    decanting a portion of the aqueous layer from the mixture;
    conveying the organic layer to a distillation column;
    forming an azeotropic mixture of 1-chloro-3,3,3-trifluoropropene and water in the distillation column;
    removing the azeotropic mixture from the distillation column as an overhead stream; and
    removing substantially pure 1-chloro-3,3,3-trifluoropropene from the bottoms of the distillation column.

10. The method of claim 9, wherein the substantially pure 1-chloro-3,3,3-trifluoropropene removed from the distillation column contains less than about 100 ppm of water by weight.

11. The method of claim 10, wherein the substantially pure 1-chloro-3,3,3-trifluoropropene removed from the distillation column contains less than about 40 ppm of water by weight.

12. The method of claim 11, wherein the substantially pure 1-chloro-3,3,3-trifluoropropene removed from the distillation column contains less than about 20 ppm of water by weight.

13. The method of claim 9, wherein the azeotropic mixture comprises from about 0.05 wt. % to about 30 wt. % water and from about 70 wt. % to about 99.95 wt. % 1-chloro-3,3,3-trifluoropropene, based on the combined weight of water and 1-chloro-3,3,3-trifluoropropene.

14. The method of claim 10, wherein the azeotropic mixture comprises from about 0.05 wt. % to about 14 wt. % water and from about 86 wt. % to about 99.95 wt. % 1-chloro-3,3,3-trifluoropropene, based on the combined weight of water and 1-chloro-3,3,3-trifluoropropene.

15. The method of claim 9, wherein the azeotropic mixture has a boiling point of about 17.4° C.±1° C. at a pressure of about 14.7 psia.

16. The method of claim 11, wherein the substantially pure 1-chloro-3,3,3-trifluoropropene removed from the distillation column contains between about 10 ppm of water by weight and about 40 ppm of water by weight.

17. The method of claim 16, wherein the substantially pure 1-chloro-3,3,3-trifluoropropene removed from the distillation column contains between about 10 ppm of water by weight and about 30 ppm of water by weight.

18. The method of claim 17, wherein the substantially pure 1-chloro-3,3,3-trifluoropropene removed from the distillation column contains between about 15 ppm of water by weight and about 20 ppm of water by weight.

19. The method of claim 16, wherein the substantially pure 1-chloro-3,3,3-trifluoropropene removed from the distillation column contains between about 11 ppm of water by weight and about 20 ppm of water by weight.

20. The method of claim 9, wherein the azeotropic mixture consists essentially of 1-chloro-3,3,3-trifluoropropene and water.

* * * * *